United States Patent
Remde

(10) Patent No.: US 7,881,883 B2
(45) Date of Patent: Feb. 1, 2011

(54) DEVICE AND METHOD FOR THE DETECTION OF AN OCCLUSION

(75) Inventor: Axel Remde, Lutzelfluh-Goldbach (CH)

(73) Assignee: Roche Diagnostics International AG, Steinhausen (CH)

( * ) Notice: Subject to any disclaimer, the term of this patent is extended or adjusted under 35 U.S.C. 154(b) by 959 days.

(21) Appl. No.: 11/549,195

(22) Filed: Oct. 13, 2006

(65) Prior Publication Data

US 2007/0270747 A1 Nov. 22, 2007

Related U.S. Application Data

(63) Continuation of application No. PCT/EP2005/003446, filed on Apr. 1, 2005.

(30) Foreign Application Priority Data

Apr. 20, 2004 (DE) .................. 10 2004 019 053

(51) Int. Cl.
G01F 15/02 (2006.01)

(52) U.S. Cl. ..................... 702/45; 702/47; 702/179; 702/182

(58) Field of Classification Search ............ 702/12, 702/19, 45, 50, 100, 114, 138; 210/646; 600/454, 547, 561; 604/4, 131
See application file for complete search history.

(56) References Cited

U.S. PATENT DOCUMENTS

| | | | |
|---|---|---|---|
| 4,882,575 A | 11/1989 | Kawahara | |
| 5,096,385 A | 3/1992 | Georgi et al. | |
| 5,501,665 A | 3/1996 | Jhuboo et al. | |
| 5,647,853 A | 7/1997 | Feldmann et al. | |
| 5,676,644 A * | 10/1997 | Toavs et al. | 604/6.11 |
| 5,808,203 A | 9/1998 | Nolan, Jr. et al. | |
| 5,858,239 A * | 1/1999 | Kenley et al. | 210/646 |
| 5,906,589 A | 5/1999 | Gordon et al. | |
| 5,967,986 A * | 10/1999 | Cimochowski et al. | 600/454 |
| 6,416,291 B1 | 7/2002 | Butterfield et al. | |
| 7,128,727 B2 * | 10/2006 | Flaherty et al. | 604/131 |
| 7,184,820 B2 * | 2/2007 | Jersey-Willuhn et al. | 600/547 |
| 2003/0073954 A1 | 4/2003 | Moberg et al. | |
| 2003/0216663 A1 | 11/2003 | Jersey-Willuhn et al. | |

FOREIGN PATENT DOCUMENTS

| | | |
|---|---|---|
| DE | 198 40 992 | 3/2000 |
| JP | 63-192451 | 8/1988 |
| JP | 2000-503249 | 3/2000 |
| JP | 2000-504965 | 4/2000 |
| WO | 01/72357 | 4/2001 |

OTHER PUBLICATIONS

H. Mouss et al., Test of Page-Hincley, an Approach for Fault Detection in an Agro-Alimentary Production System, 2004, 5th Asian Control Conference, IEEE, pp. 815-818.*

* cited by examiner

*Primary Examiner*—Eliseo Ramos Feliciano
*Assistant Examiner*—Felix E Suarez
(74) *Attorney, Agent, or Firm*—Dorsey & Whitney LLP

(57) ABSTRACT

A method for detecting occlusions including providing a signal that characterizes a conveying status of a fluid, and determining from a difference between two such signals whether an occlusion has occurred. The invention encompasses a device for detecting an occlusion including a sensor for sensing a fluid flow parameter and/or an operational parameter of the device and an evaluation unit for processing the output of the sensor.

10 Claims, 4 Drawing Sheets

DEVICE AND METHOD FOR THE DETECTION OF AN OCCLUSION

CROSS-REFERENCE TO RELATED APPLICATION(S)

This application is a continuation of International Patent Application No. PCT/EP2005/003446, filed on Apr. 1, 2005, which claims priority to German Application No. 10 2004 019 053.4, filed on Apr. 20, 2004, both of which are incorporated herein by reference.

BACKGROUND

The present invention relates to devices for delivering, dispensing, injecting, administering or infusing substances, and to methods of making and using such devices. More particularly, it relates to a device and method for detecting an occlusion in such devices, for example, in infusion pumps. Occlusions, i.e., blockages in a flow path or fluid path, must be detected as quickly as possible in portable infusion pumps to minimize the time during which, erroneously, no medicament is discharged.

The invention relates more particularly to the field of miniaturized infusion pumps which are worn by the patient permanently on his body and which ensure a (quasi)continuous delivery of medicament. A particular danger of these systems lies in possible blockages (occlusions), either of the catheter or of the infusion cannula. The resulting interruption in delivery can, if it continues, lead to a potentially life-threatening situation for the patient. If a temporary occlusion resolves itself before it is detected, the whole quantity of medicament that has been held back could be dispensed spontaneously. This overdose can likewise lead to a dangerous situation. This problem is known, for example, in the treatment of diabetes mellitus using continuous subcutaneous insulin infusion (CSII).

The detection of occlusions in portable infusion pumps takes place in the present systems by means of measuring the motor current and/or the reaction force in the gear mechanism by means of a force sensor, for example as is described in WO 0172357, U.S. Pat. No. 5,647,853 or DE 19840992. The evaluation is principally obtained by threshold comparisons for the force F exerted by the drive on the ampule stopper, or a numerical approximation of its time derivation dF/dt, for example by calculation of regression lines. These methods entail a long detection delay, because the measurements reflect an occlusion only slowly and they are dependent on a whole series of influencing variables, which can generally fluctuate within a wide range (e.g., friction of gear mechanism and ampule stopper), so that the chosen threshold values have to be high to avoid incorrect detections. With the known methods, a significant reduction in the detection delay would therefore require control of all the influencing variables in very narrow limits and would therefore be technically complex and expensive.

SUMMARY

In one embodiment, the present invention comprises a method for detecting an occlusion comprising the steps of providing a signal that characterizes a conveying status of a fluid, and comparing the signal and another signal, wherein a difference between the signal and the another signal indicates whether an occlusion has occurred. In some embodiments, the method comprises using the Page-Hinkley stopping rule, a cumulative sum stopping test, a cumulative likelihood ratio algorithm or other suitable algorithm.

In one embodiment, the present invention comprises a device for detecting an occlusion associated with a fluid flow, the device comprising a sensor for sensing and/or measuring at least one of a fluid pressure of the fluid and a force characteristic of a conveying status of the fluid and providing and/or communicating a signal, and an evaluation unit for comparing the signal and another value, wherein the difference between the signal and the value indicates whether an occlusion has occurred. In some embodiments, other characteristics or parameters of the function or operation of the device may be used to determine or calculate whether an occlusion is present or has occurred.

In one embodiment, the present invention comprises a method for detecting occlusions comprising providing a signal that characterizes a conveying status of a fluid, and determining from a difference between two such signals whether an occlusion has occurred.

In some embodiments, the present invention comprises a device for detecting an occlusion including a sensor for sensing a fluid flow parameter and/or an operational parameter of the device and an evaluation unit for processing the output of the sensor.

In one embodiment, the method according to the present invention for signal evaluation and generation of an occlusion alarm can also be used in connection with what is purely a force measurement. For this purpose, the required control system can be integrated into firmware associated with devices such as insulin pumps, for example.

One field of use of the present invention is in continuous subcutaneous insulin infusion (CSII) as follows:

The patient is alerted more quickly after an occlusion occurs and can take suitable measures to rectify it (e.g., change the catheter) and, if appropriate, to correct an already elevated blood glucose level before a potentially dangerous situation develops. The present invention thus improves the safety of the treatment.

Since the time needed for occlusion detection increases as the delivery rate decreases, it is particularly critical in patients with a very low medication requirement (e.g., children). In these case, safe treatment is really only possible using a rapid detection method.

It is, in principle, desirable to use fairly high concentrations of insulin, but this is presently thwarted, inter alia, by the resulting extension of the delay between occurrence and detection of occlusions. The method of the present invention permits an acceptable speed of detection, even at higher insulin concentrations, so that smaller and more discreet pumps can be used.

The method for rapid occlusion detection in accordance with the present invention is based on real-time evaluation of a measurement signal, a sensed value or a fluid flow characteristic or parameter which mirrors an occlusion, for example by an (almost) abrupt change. In some embodiments, fluid pressure is suitable as a measurement signal, because it mirrors the occurrence of an occlusion quickly and with greater sensitivity than other measurement signals. In some preferred embodiments, the pressure may be measured at the pump outlet, with a commercially available pressure sensor (e.g., a piezoresistive Wheatstone bridge). Other fluid flow parameters or measurement signals or values may be used, separately or in conjunction with a pressure measurement or each other, as well.

DETAILED DESCRIPTION OF THE DRAWINGS

FIG. 2a is a schematic representation of the fluid pressure at a pump outlet when an occlusion occurs.

FIG. 2b shows the time derivation of the pressure of FIG. 2a.

DETAILED DESCRIPTION OF THE DRAWINGS

Figure 1:
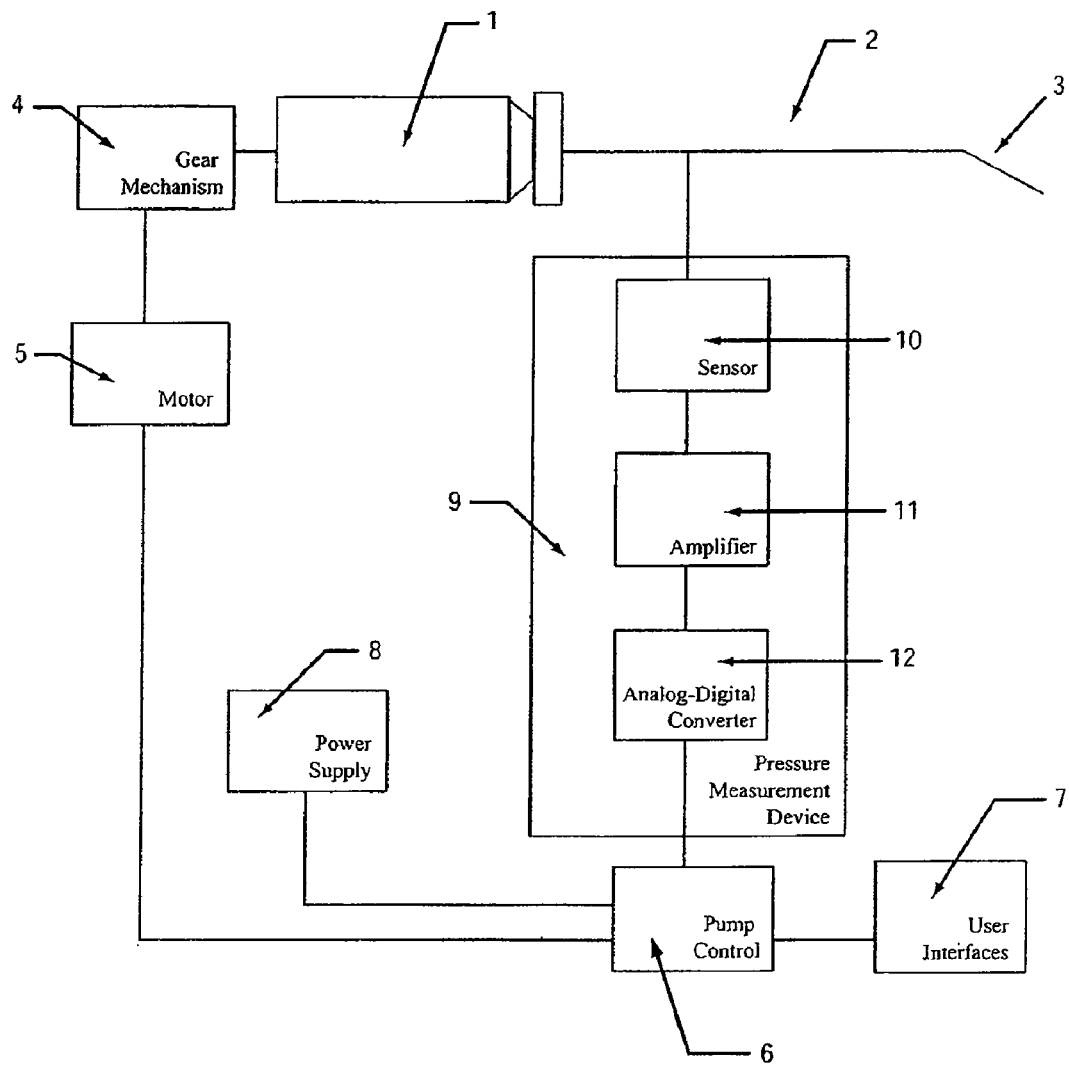
FIG. 1 depicts an embodiment of a device in accordance with the present invention.

FIG. 1 shows the relevant components of an exemplary system or device in accordance with the present invention. The exemplary system or device comprises a medicament reservoir 1, catheter 2, cannula 3, gear mechanism 4, motor 5, pump control 6, user interfaces 7 (for example, a display, buzzer, vibrator, keyboard, etc.), power supply 8, and pressure measurement device 9. The measurement signal provided by a sensor 10, for example in the form of a voltage, is processed by an amplifier 11 with downstream analog-digital converter 12. The sensor 10 can, for example, measure the fluid pressure in the ampule 1, catheter 2, cannula 3 or other suitable location or structure associated with the system or device.

With regard to fastening, mounting, attaching or connecting components of devices or systems in accordance with the present invention, unless specifically described otherwise, conventional fasteners, e.g., screws, pins, etc., may be used. Other suitable fastening or attachment means include friction fitting, adhesives, welding and soldering, the latter particularly with regard to electrical or processing components. Any suitable electronic, electrical, communication, computer or processing components may be used, including any suitable electrical components and circuitry, wires, wireless components, inputs, outputs, sensors, chips, boards, microprocessing or control system components, software, firmware, hardware, etc.

While fluid pressure is one suitable criterion, parameter or characteristic for use in the present invention, the evaluation method of the present invention can also be used with or for other measurement signals, for example, a gear mechanism reaction force F. Adaptation to other measurement signals using other suitable sensors, for example for pressure measurement or force measurement, is easily possible on the basis of the description given here.

In one embodiment, for the method for occlusion detection in accordance with the present invention, continuous recording of the pressure signal is advantageous, but not essential. Instead, for example, individual measurements can be made at defined times, for example directly before or after a medicament discharge or at continuous intervals. The exact choice of the measurement times is not significant for the occlusion detection. To keep the power consumption of the measurement device 9 to a minimum, it does not have to be operated continuously, and instead can be powered by the pump control 6, for example with energy from the supply 8 only at the measurement times.

The signal evaluation is described below on the basis of scanning being done at a constant scanning interval $\Delta t$. The same method can be used in the case of a variable scanning interval. In this case, only the pressure differences $p_i - p_{i-1}$ (with 1 as continuous measurement index) and the associated difference quotients $$\frac{p_i - p_{i-1}}{t_i - t_{i-1}}$$

can be used.

In some preferred embodiments the occlusion detection is carried out using an algorithm on the microprocessor of the pump control 6. However, it can also be done using specialized hardware components or peripheral devices.

Figure 2:
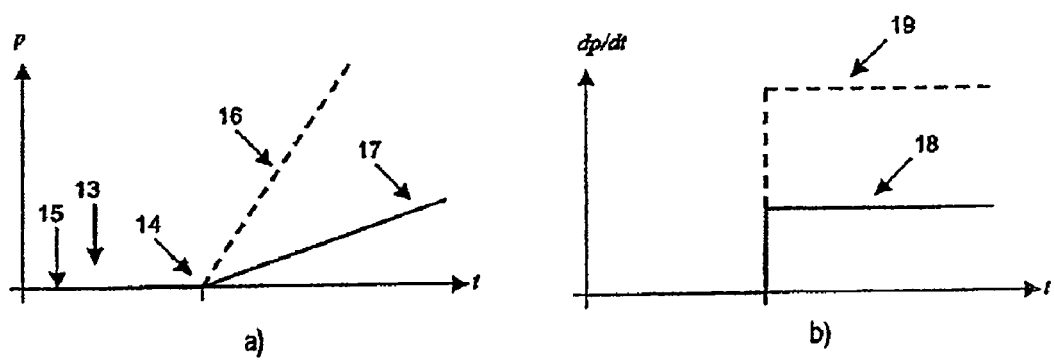

FIG. 2a is a schematic representation of the fluid pressure at the pump outlet 13 when an occlusion occurs at the time $t_{occlusion}$ 14. FIG. 2b shows the time derivation of the pressure. Before occurrence of the occlusion, the pressure (relative to the atmospheric pressure) is on average zero (15), after which it rises approximately linearly, the rise per unit of time being less at a low delivery rate (16) than at a high delivery rate (17), as can be seen from the respective time derivation (18, 19).

In practice, however, the pressure signal is affected by a large number of high-frequency and low-frequency disturbances, which can be of the same order of magnitude as the pressure rise at which an alarm is intended to sound in the event of an occlusion. A typical characteristic in particular of the permanent use of portable infusion pumps is that the geodetic heights $h_{pump}$ of the pump and of the infusion site (seat of the cannula) $h_{infusion}$ are not identical and are also not constant (e.g. when operating the pump, changing the infusion site, lying down, etc.). Because of the hydrostatic pressure of the medicament column in the catheter, the height difference $\Delta h = h_{pump} - h_{infusion}$ results in a pressure signal proportional to this.

Figure 3:
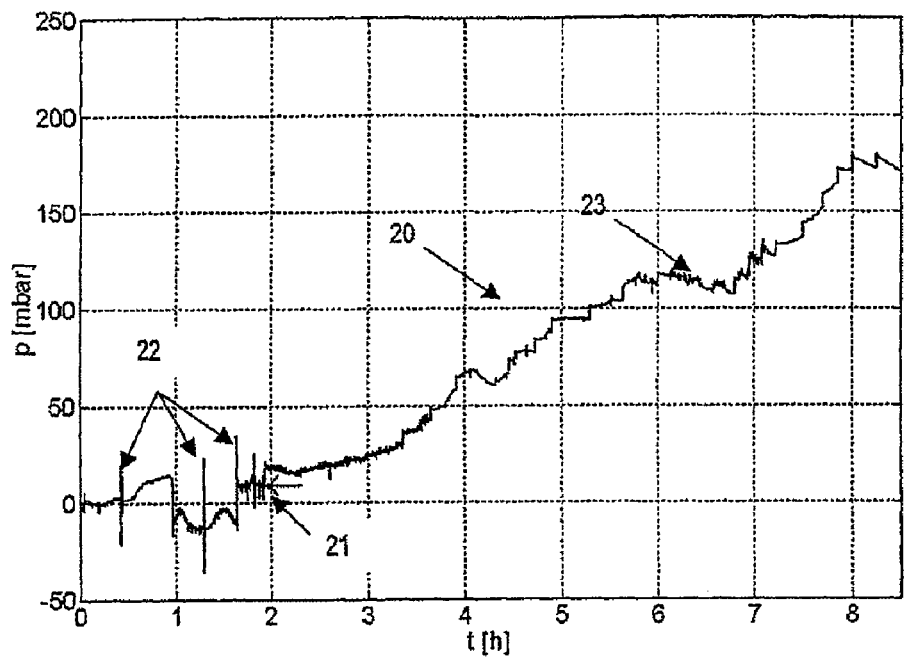
FIG. 3 shows an example of a pressure profile.

FIG. 3 shows an example of a pressure profile (20) which occurs under real conditions at a delivery rate of 1 μl/h with occlusion time (21). Distinct fluctuations with pressure peaks (22) exist before the start of the occlusion, and there are also quite long phases of constant or falling pressure (23) after the start of the occlusion.

It is therefore provided, in the present invention, that instead of evaluating the direct pressure signal p, suitable (nonlinear) filtering is used to determine a modified pressure signal $\tilde{p} = \tilde{f}(p)$ that comprises the following features:

The continuous pressure rise occurring in the event of an occlusion is transferred substantially free of delay and free of attenuation from p to $\tilde{p}$.

Other fluctuations and sudden changes are so strongly attenuated that they do not lead to an error alarm.

Simple (linear) low-pass filters are not suitable for this purpose, because here the pressure rise of an occlusion would transfer only very slowly.

In one embodiment, the filtering comprises limiting the pressure rise $\Delta p = p_i - p_{i-1}$ between the scans, with the modified pressure signal being calculated as follows:

$\tilde{p}_0 = 0$ (initialization)

$\Delta \tilde{p}_i = f(\Delta p_i)$ $\tilde{p}_i = \tilde{p}_{i-1} + \Delta \tilde{p}_i$ Here, $f$ is the transfer function limiting the pressure rise. In the simplest case, $f$ is a non-rectilinear function according to FIG. 3, consisting of three linear segments with gradients zero and one. The threshold value $p_{limit}$ defines the maximum change in the modified pressure signal per scanning interval. This is to be chosen such that the pressure surge $\Delta p_{occlusion}$ occurring at each delivery in the event of an occlusion is transferred as completely as possible, on the other hand a sudden rise or drop of the pump causes no response of the subsequent detection algorithm. If, for occlusion detection, a simple threshold value $\lambda$ is applied to the modified pressure signal, this accordingly must mean $\Delta p_{limit} \geq \Delta p_{occlusion}$ $c \Delta p_{limit} < \lambda$ Here, c is a constant determined by the required detection safety and by the admissible rate of error alarms. Since $\Delta p_{occlusion}$ rises with increasing delivery rate, $\Delta p_{limit}$ should also be chosen to grow with increasing delivery rate.

Figure 4:
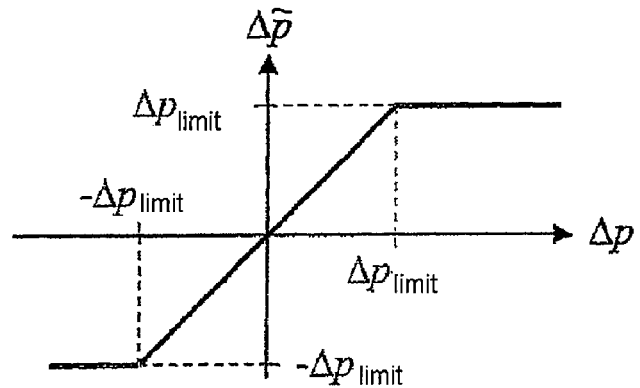
FIG. 4 shows another example of a pressure profile.
Figure 5:
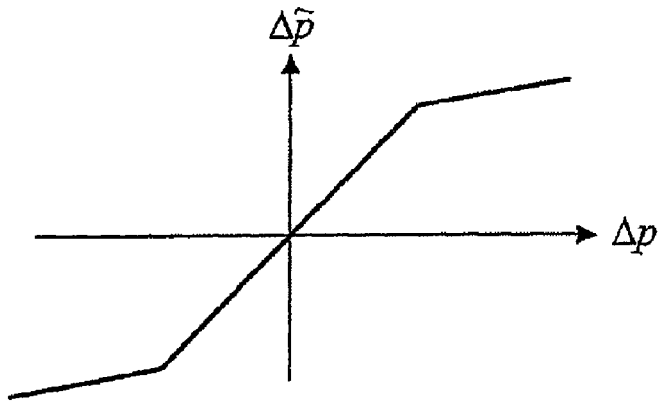
FIG. 5 shows another example of a pressure profile.

In addition to the function shown in FIG. 4, $f$ can also be another linear function with $$\frac{\Delta \tilde{p}}{\Delta p} = 1 \text{ for } |\Delta p| \leq \Delta p_{limit}$$

$$0 < \frac{\Delta \tilde{p}}{\Delta p} < \text{ for } |\Delta p| > \Delta p_{limit}$$

according to FIG. 5, as a result of which the choice of $\Delta p_{occlusion}$ is less critical. Alternatively, it is possible to use functions of similar profile that can be differentiated at all times.

Figure 6:
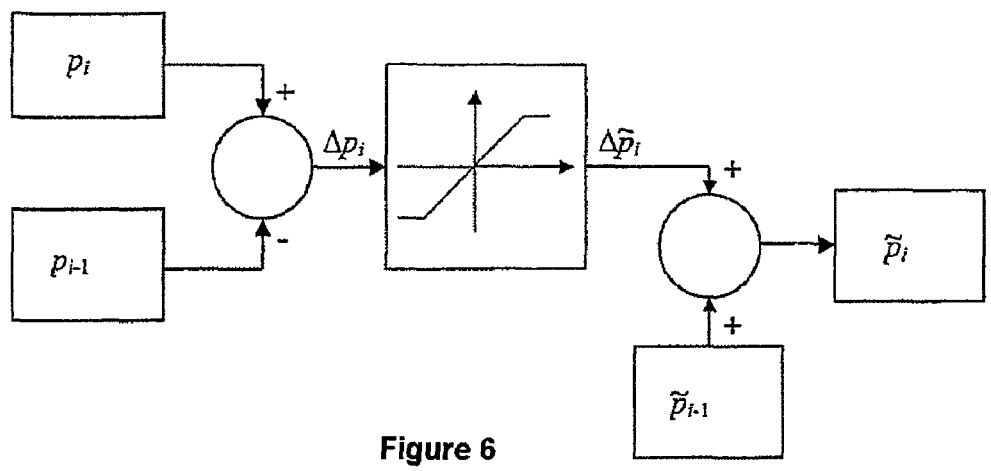
FIG. 6 shows a signal flow for obtaining a modified pressure signal.
Figure 7:
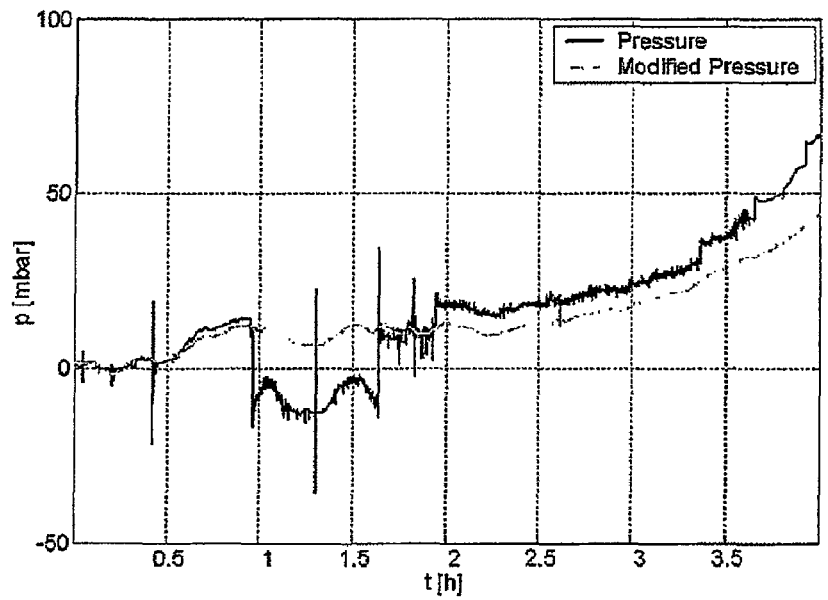
FIG. 7 depicts the behaviour of pressure and modified pressure associated with an occlusion detection.

FIG. 6 shows the signal flow for obtaining the modified pressure signal. The implementation of $f$ is done by analytic functions or by a look-up table.

Figure 8:
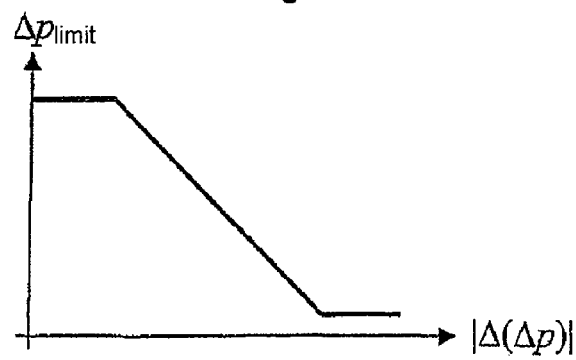
FIG. 8 depicts a function useful in assessing a disturbance level.

In the formulation given above, $\Delta p_{limit}$ and thus the transfer function $f$ is defined exclusively on the basis of the actual delivery rate. To increase the detection safety, however, it is recommended to adapt $f$ by inclusion of the noise and disturbance level. In this way, it is possible to ensure that occlusions are detected as quickly as possible at low disturbance level (during restful activities, at night, etc.) without error alarms occurring at a high disturbance level (for example during sports activities). A universal and simple measure that is suitable for the disturbance level is the second second difference $\Delta(\Delta p)$ with $\Delta(\Delta p)_i = \Delta p_i - \Delta p_{i-1} = p_i - 2p_{i-1} + p_{i-2}$.

which represent an approximation of the second time derivation. The smaller ($\Delta p$) is, the greater $\Delta p_{limit}$ must be chosen.[1] The choice of $\Delta p_{limit} = g(\Delta(\Delta p))$ is done with g according to FIG. 8 or a similar function. It is also possible not to determine $\Delta p_{limit}$ from a single value of $\Delta(\Delta p)$, but instead to filter for ($\Delta(\Delta p)$). This can be done by a sliding mean value, other linear or nonlinear low-pass filter or other suitable methods.

[1] Determining the disturbance level based on the simple difference $\Delta p$ is not suitable, since otherwise the (approximately) constant pressure rise per scan would not transfer completely in the event of an occlusion.

In the pressure signal $\tilde{p}$ modified in this way, occlusion detection can be done very easily, for example by a threshold value $\lambda$, with an occlusion alarm being triggered when the latter is exceeded. $\lambda$ can be fixed or can also be chosen as a function of the delivery rate.

In some embodiments of the present invention, it is advantageous, however, instead of using a direct threshold value for $\tilde{p}$, to use the recursive calculation of a function U (with initialization $U_1 = 0$) according to the following formula:

$$U_i = U_{i-1} + (\Delta \tilde{p}_i - k)$$

$$m_i = \min_{1 \leq k \leq i} U_k$$

$$R_i = U_i - m_i$$

Here, k is the minimal pressure rise (dependent on the delivery rate) per scan in the event of an occlusion. A pressure rise with pressure differences that on average lie below 2k (e.g. by sensor drift) leads with certainty not to an occlusion alarm. The occlusion detection is done by comparison of R with a threshold value $\lambda$.

$$\begin{cases} \text{if } R_i \leq \lambda: & \text{no occlusion} \\ \text{if } R_i > \lambda: & \text{occlusion} \end{cases}$$

The robustness of this approach can be seen from the following consideration. As long as there is no occlusion, the terms $\Delta p_i - k$ are negative on average, so that the $U_i$ also become increasingly negative (even though noises also result in positive summands). Accordingly, minU also becomes more and more negative and does not differ significantly from U. (Without outliers toward the top this would mean $m_i = U_i$ at each time). Therefore, R is always positive and approximately zero. Individual "outliers toward the top" for $\Delta \tilde{p}$ do not lead to a significant increase in U and therefore also do not lead to an erroneous occlusion detection.

After occurrence of an occlusion, the terms $\Delta p_i - k$ are positive on average, so that U also increases on average (even though noises also result in negative summands). Since minU no longer changes, R now also rises, the gradient (because of k) being slightly less than that of $\tilde{p}$. Individual "outliers toward the bottom" for $\Delta \tilde{p}$ as a whole do not lead to a significant fall of U.

Figure 9:
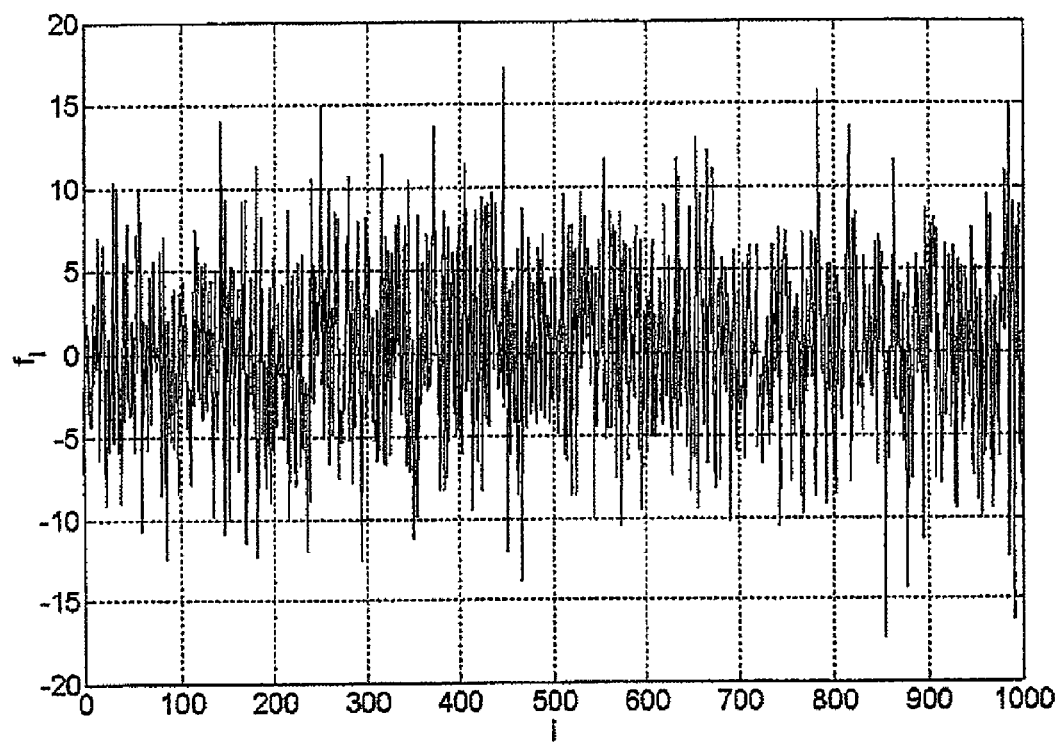
FIG. 9 depicts a general function $f$ corresponding to an occlusion detection.
Figure 10:
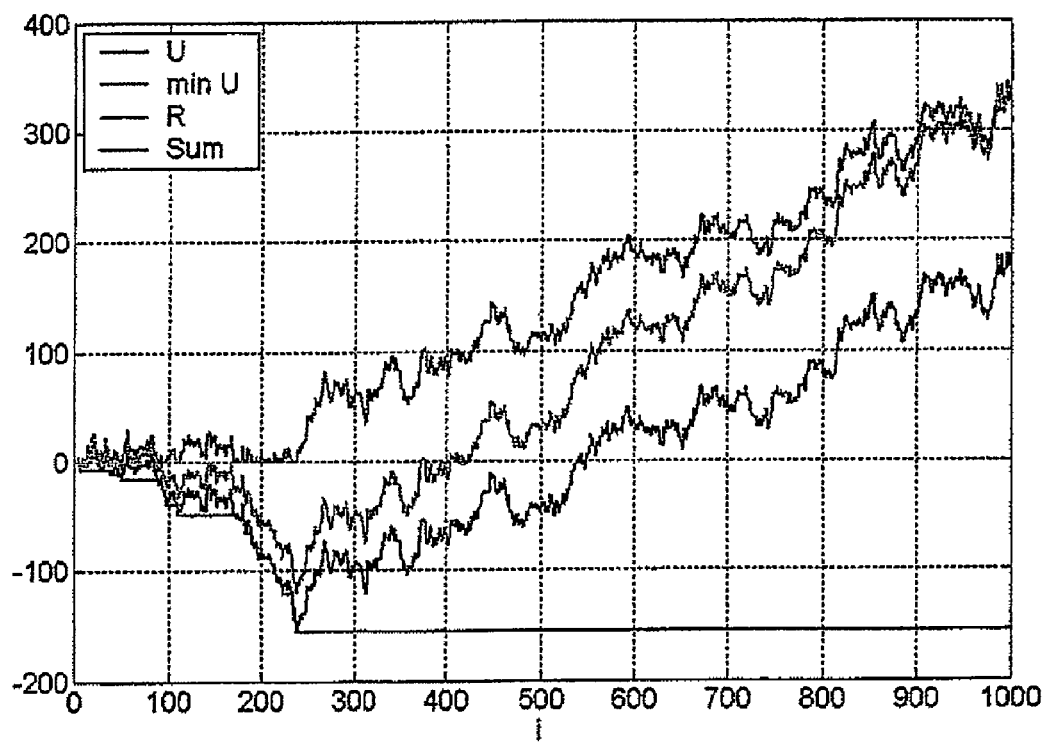
FIG. 10 depicts the behaviour of pressure and modified pressure associated with an occlusion detection.

In FIG. 9 and FIG. 10, the behavior is shown by way of an example. FIG. 9 first shows a general function $f$ (which corresponds to the $\Delta \tilde{p}$ of the occlusion detection). Initially the mean value is $\bar{f}_1 = 0$, the superposed normally distributed noise has a standard deviation of $\sigma = 5$. At the index $i_{jump} = 300$, the mean value jumps to $\bar{f}_2 = 0.5$ (start of an occlusion), while the noise remains unchanged. FIG. 10 shows the profile of U (blue), m=minU (green) and R (red). For comparison, the sum over the $f_i$ (turquoise, corresponds to $\tilde{p}$) is additionally shown. It is clear that U at first decreases on average and reaches its minimum at $i \approx 250$ (without noise it would be i=300), and R is initially very small. For $i > i_{jump}$, U and thus also R rises continuously. For i=400, R is already clearly above the greatest value before the jump, whereas this still applies for the sum of $f_i$ so that R is more favorable for a rapid detection. As time passes, both functions further approximate to each other.[2] This method is known from the literature as the Page-Hinkley stopping rule, and it has been shown that, assuming normally distributed noise, it minimizes the mean detection time.

[2] Because of $k_i$ the sum of $f_i$ would also at some point be greater than R.

To permit occlusion detection even under very unfavorable conditions in which the pressure signal cannot be evaluated because of extreme disturbances, it is possible to couple the approach proposed here with one or more of the hitherto used methods (measurement of motor current or gear mechanism reaction force).

Two exemplary procedures are:

The different methods for occlusion detection work in parallel and independently of one another. Occlusion is always assumed when it has been detected by one of the methods (OR function).

The disturbance level of the pressure signal is monitored permanently (e.g. by evaluating the second time difference, see above). If the disturbance level exceeds a threshold value above which a reliable evaluation is no longer guaranteed, the pressure-based occlusion measurement is temporarily deactivated to avoid incorrect alarms, and instead another method is employed, with the disturbance level of the pressure signal continuing to be measured. If it drops below a given threshold value, a change is made back to the more sensitive pressure-based occlusion detection.

One advantageous embodiment is one in which both alternatives are combined. Here, the different methods work in parallel. The starting signals of the individual methods (e.g. R and F in the case of measuring pressure and the gear mechanism reaction force) are combined with the aid of fuzzy AND logic operation. The pressure measurement is weighted more strongly compared to the force measurement, the lower the noise signal. The two abovementioned alternatives provide limit values for very low and very high disturbances of the pressure signal.

It is also possible to generate further occlusion criteria from the pressure signal (e.g., gradient of a linear or nonlinear regression function) and combine them with embodiments of the present invention or provide additional embodiments of the method in accordance with the present invention by means of a fuzzy AND logic operation.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for detecting an occlusion, said method comprising the steps of:
    providing a signal that corresponds to a fluid pressure in at least one of an ampoule, a catheter, and a cannula of a fluid that is being at least one of infused, administered, and injected;
    filtering the signal, wherein filtering comprises modifying the signal by applying a transfer function to the signal such that a pressure rise between chronologically successive readings of the signal is limited; and
    comparing the filtered signal and a reference signal,
    determining whether an occlusion in a flow path of the fluid has occurred based on a difference between the filtered signal and the reference signal.

2. The method as claimed in claim 1, wherein the signal corresponds to a direct measure of the fluid pressure.

3. The method as claimed in claim 2, wherein the signal is generated by a pressure sensor positioned proximate a pump outlet.

4. The method as claimed in claim 1, wherein the signal corresponds to an indirect measure of the fluid pressure.

5. The method as claimed in claim 4, wherein the signal is generated by a force sensor that is measuring a gear mechanism reaction force.

6. The method as claimed in claim 1, wherein the providing of the signal is carried out either continuously or discretely.

7. The method as claimed in claim 1, wherein the step of comparing the filtered signal and the reference signal comprises taking into account a respective delivery rate.

8. The method as claimed in claim 1, wherein at least one of the steps of filtering the signal and comparing the filtered signal and the reference signal comprises taking into account a disturbance level of the fluid pressure.

9. The method as claimed in claim 1, wherein at least one of the steps of filtering the signal and comparing the filtered signal and the reference signal comprises applying the Page-Hinkley stopping rule.

10. A device for detecting an occlusion, the device comprising
    a sensor for sensing a fluid pressure in at least one of an ampoule, a catheter, and a cannula of a fluid that is being at least one of infused, administered, and injected, and
    a processor coupled to the sensor,
    wherein the processor is adapted to execute computer-implemented instructions to:
        filter the signal, wherein filtering comprises modifying the signal by applying a transfer function to the signal such that a pressure rise between chronologically successive readings of the signal is limited,
        compare the filtered signal and a reference signal, and
        determine whether an occlusion in a flow path of the fluid has occurred based on a difference between the filtered signal and the reference signal.

* * * * *